US010010390B2

(12) United States Patent
Fritsch (10) Patent No.: US 10,010,390 B2
(45) Date of Patent: Jul. 3, 2018

(54) ORAL CARE IMPLEMENT AND ORAL CARE DEVICE

(71) Applicant: Braun GmbH, Kronberg (DE)

(72) Inventor: Thomas Fritsch, Eppstein (DE)

(73) Assignee: BRAUN GMBH, Kronberg (DE)

( * ) Notice: Subject to any disclaimer, the term of this patent is extended or adjusted under 35 U.S.C. 154(b) by 390 days.

(21) Appl. No.: 14/965,609

(22) Filed: Dec. 10, 2015

(65) Prior Publication Data

US 2016/0166366 A1 Jun. 16, 2016

(30) Foreign Application Priority Data

Dec. 10, 2014 (EP) .................................. 14197153
Nov. 10, 2015 (EP) .................................. 15193878

(51) Int. Cl.
*A61C 17/22* (2006.01)
*A61C 17/32* (2006.01)
*A61C 17/34* (2006.01)

(52) U.S. Cl.
CPC ........ *A61C 17/222* (2013.01); *A61C 17/3436* (2013.01); *A61C 17/3463* (2013.01); *A61C 17/3472* (2013.01)

(58) Field of Classification Search
CPC .............. A61C 17/222; A61C 17/3436; A61C 17/3454; A61C 17/3463; A61C 17/3472
USPC ................................................ 15/22.1, 167.1
See application file for complete search history.

(56) References Cited

U.S. PATENT DOCUMENTS

| 5,974,615 | A | * | 11/1999 | Schwarz-Hartmann |
| | | | | ........................ A61C 17/3472 |
| | | | | 15/22.1 |
| 6,574,820 | B1 | * | 6/2003 | DePuydt .............. A61C 15/047 |
| | | | | 15/22.1 |
| 2003/0066145 | A1 | * | 4/2003 | Prineppi ................ A61C 17/22 |
| | | | | 15/22.1 |
| 2003/0163882 | A1 | * | 9/2003 | Blaustein ............. A46B 13/008 |
| | | | | 15/22.2 |
| 2004/0060137 | A1 | * | 4/2004 | Eliav ...................... A61C 17/22 |
| | | | | 15/22.1 |
| 2005/0011023 | A1 | | 1/2005 | Chan |
| 2006/0010623 | A1 | * | 1/2006 | Crossman .......... A61C 17/3472 |
| | | | | 15/22.1 |
| 2006/0048314 | A1 | * | 3/2006 | Kressner ............ A61C 17/3454 |
| | | | | 15/22.1 |
| 2007/0251033 | A1 | * | 11/2007 | Brown ................. A61C 17/349 |
| | | | | 15/22.1 |

(Continued)

FOREIGN PATENT DOCUMENTS

| EP | 1093770 | 4/2001 |
| EP | 2428184 | 3/2012 |
| WO | WO2004028293 | 4/2004 |

*Primary Examiner* — Weilun Lo (57) ABSTRACT

An oral care implement having a housing, a functional element mounted at the housing for driven oscillatory rotation relative to the housing around a rotation axis, at least one rocking lever that is on a first end pivotably supported at the housing at an essentially fixed position that is eccentric with respect to the rotation axis and the rocking lever is on a second end coupled with the functional element at a position eccentric with respect to the rotation axis such that the functional element carries the second end of the rocking lever along when it is driven into oscillatory rotation around the rotation axis, while the first end of the rocking lever is kept at its fixed position at the housing.

13 Claims, 6 Drawing Sheets

(56) References Cited

U.S. PATENT DOCUMENTS

| | | | |
|---|---|---|---|
| 2009/0183324 A1* | 7/2009 | Fischer | A61C 17/34 15/22.1 |
| 2011/0072599 A1 | 3/2011 | Brown et al. | |
| 2012/0024323 A1* | 2/2012 | Klemm | A61C 17/22 134/18 |
| 2012/0060309 A1* | 3/2012 | Kressner | A61C 17/3472 15/167.1 |
| 2012/0137452 A1* | 6/2012 | Dickie | A61C 17/349 15/22.1 |

\* cited by examiner

ORAL CARE IMPLEMENT AND ORAL CARE DEVICE

FIELD OF THE INVENTION

The present invention is concerned with an oral care implement comprising a housing and a functional element that is mounted at the housing for driven oscillatory rotation around a rotation axis. It is in particular concerned with such oral care implements, where the functional element is arranged for an additional motion.

BACKGROUND OF THE INVENTION

It is known that oral care implements such as replacement brush heads comprise a housing and a functional element (e.g. a brush head) that is mounted at the housing for driven oscillatory rotation around a rotation axis. It is also known that the functional element can be arranged for an additional motion such as a linear oscillating motion along the longitudinal axis of the oral care implement as is generally discussed in document EP 2 428 184 A1. Such additional motions can provide enhanced oral care properties, e.g. enhanced cleaning properties in case of an electric toothbrush.

It is an object of the present disclosure to provide an oral care implement that is an improvement over known oral care implements or that is at least an alternative to known oral care implements.

SUMMARY OF THE INVENTION

In accordance with one aspect there is provided an oral care implement having a housing, a functional element mounted at the housing for driven oscillatory rotation relative to the housing around a rotation axis, at least one rocking lever that is on a first end pivotably supported at the housing at an essentially fixed position that is eccentric with respect to the rotation axis and the rocking lever is on a second end coupled with the functional element at a position eccentric with respect to the rotation axis such that the functional element carries the second end of the rocking lever along when it is driven into oscillatory rotation around the rotation axis, while the first end of the rocking lever is kept at its fixed position at the housing.

In accordance with one aspect there is provided an oral care device that comprises a housing, a functional element mounted at the housing for driven oscillatory rotation relative to the housing around a rotation axis, at least one rocking lever that is on a first end pivotably supported at the housing at an essentially fixed position that is eccentric with respect to the rotation axis and the rocking lever is on a second end coupled with the functional element at a position eccentric with respect to the rotation axis such that the functional element carries the second end of the rocking lever along when it is driven into oscillatory rotation around the rotation axis, while the first end of the rocking lever is kept at its fixed position at the housing and a handle that is either integral with the housing or to which the housing is detachably connected.

BRIEF DESCRIPTION OF THE DRAWINGS

The present invention is further elucidated by a detailed description of example embodiments of the proposed oral care implement and oral care device, where particular reference is made to figures. In the figures

DETAILED DESCRIPTION OF THE INVENTION

An oral care implement or oral care device as provided by the present disclosure has a functional element mounted at a housing, which functional element is arranged for driven oscillatory rotation around a rotation axis relative to the housing and that is further arranged for an additional linear oscillatory motion along the rotation axis of the functional element (also called a poking motion) relative to the housing. The rotation axis may in particular be defined by a rotation axle that is supported at the housing and around which the functional element can rotate when driven into motion.

The oral care implement comprises a rocking lever that is arranged between the housing and the functional element so that the rocking lever defines a distance between housing and functional element in the direction of the rotation axis. The rocking lever is on a first end pivotably mounted at an essentially fixed position at the housing (i.e. said first end is essentially kept fixed with respect to the housing when the functional element is driven into motion). The rocking lever is on a second end essentially fixedly coupled with the functional element (i.e. said second end is essentially kept fixed with respect to the functional element when the functional element is driven into motion). When the functional element is driven into an oscillatory rotation, the distance defined by the rocking lever in direction of the rotation axis is varied as due to the movement of the functional element and the fixation of the first and second ends at the housing and the functional element, respectively, the inclination of the rocking lever against the rotation axis is varied. The additional poking motion may then be self-induced by the at least one rocking lever or an external force (e.g. brushing force applied during regular operation) may be required to actively induce the additional poking motion. Here it is relevant whether the rocking lever is arranged to actively push and pull the functional element, whether another active element is present that supports the pulling and pushing (e.g. a spring element arranged between housing and functional element) or whether the rocking lever just provides a distance piece of varying distance. This will be discussed in more detail further below.

In order to be able to change its inclination during the driven motion of the functional element relative to the housing, the fixed positions of the first and second ends of the rocking lever at the housing and the functional element, respectively, are eccentric with respect to the rotation axis.

The functional element in accordance with the present disclosure is arranged for an oscillatory rotation around the rotation axis. This oscillation shall be considered as harmonic such that the oscillation motion is characterized by the motion of the functional element between two maximum angular elongations in clockwise and anti-clockwise direction around the rotation axis, e.g. in some embodiments the maximum elongations (maximum deflection angles) are ±20 degrees under a no-load situation. The center oscillation position is then at 0 degrees, i.e. in the middle between the two maximum elongations. When a load is applied at the functional element, the maximum elongation may break down.

A rocking lever in accordance with the present disclosure comprises a main leg and a first and a second end. The first end of the rocking lever is supported at an essentially fixed position at the housing, which position is eccentric with respect to the rotation axis of the functional element, and the second end of the rocking lever is coupled with the functional element at an essentially fixed position that is also eccentric with respect to the rotation axis of the functional element. The rocking lever extends between housing and functional element such that it has a length component in the direction of the rotation axis. In embodiments where the second end of the rocking lever is extended (e.g. where the second end comprises a crossbeam arm that extends at an angle, in particular a right angle from the main leg of the rocking lever), it is relevant where the main leg ends and where this portion of the second end is supported at the functional element. The extended second arm (e.g. the crossbeam arm) may then extend towards the rotation axis or may even cross the rotation axis, so that the rocking lever does not only apply a force to move the functional element at the eccentric bearing point but also closer to the rotation axis and potentially even symmetrically with respect to the rotation axis, which reduces the risk of canting of the functional element on a rotation axle.

Generally, the rocking lever is on the first end supported at the housing and at the second end coupled with the functional element so that when the functional element is rotated, the second end of the rocking lever is carried along relative to the first end that is fixed at the housing. As the rocking lever is an essentially straight and rigid object, this means that when the functional element is rotated, the height of the rocking lever projected onto the rotation axis changes. E.g. when the functional element is rotated so that the first end and the second end come closer to each other, the rocking lever must become erected from a more inclined orientation (where inclined is used to specify an orientation that deviates from an orientation that is parallel to the rotation axis) to a less inclined position. In some embodiments, the rocking lever may be oriented parallel to the rotation axis for a given oscillation position of the functional element (e.g. this may be the center oscillation position—the center oscillation position is then in the middle between the maximum elongations in positive and negative oscillation direction—or a maximum elongation position). In other embodiments, the rocking lever may just become erected into a least inclined orientation. This least inclined or parallel orientation of the rocking lever then defines the maximum distance that is defined by the rocking lever between the housing and the functional element. The oscillation position of maximum inclination of the rocking lever then defines the minimum distance between the housing and the functional element. The maximum elongation (maximum deflection angle) of the driven oscillatory rotation of the functional element around the rotation axis may break down under a load applied at the functional element. Then, the amplitude of the poking motion may break down as well.

In accordance with the present disclosure, the term "coupled with" used in connection with the second end of the rocking lever shall include that the second end of the rocking lever is loosely held by a supporting structure (e.g. a bearing hole) provided at the functional element, which supporting structure allows that the rocking lever can pivot in this supporting structure and that the second end of the rocking lever is essentially fixed with respect to its distance to the rotation axis, while the second end of the rocking lever may be movable in a direction parallel to the rotation axis (without decoupling from the supporting structure). It shall also include that the second end is also fixed in the movement in the direction parallel to the rotation axis. Further, it shall include that the second end of the rocking lever is realized integral with the functional element and the necessary pivoting is enabled by realizing the second end of the rocking lever as a hinge, in particular a living hinge.

Figure 1:
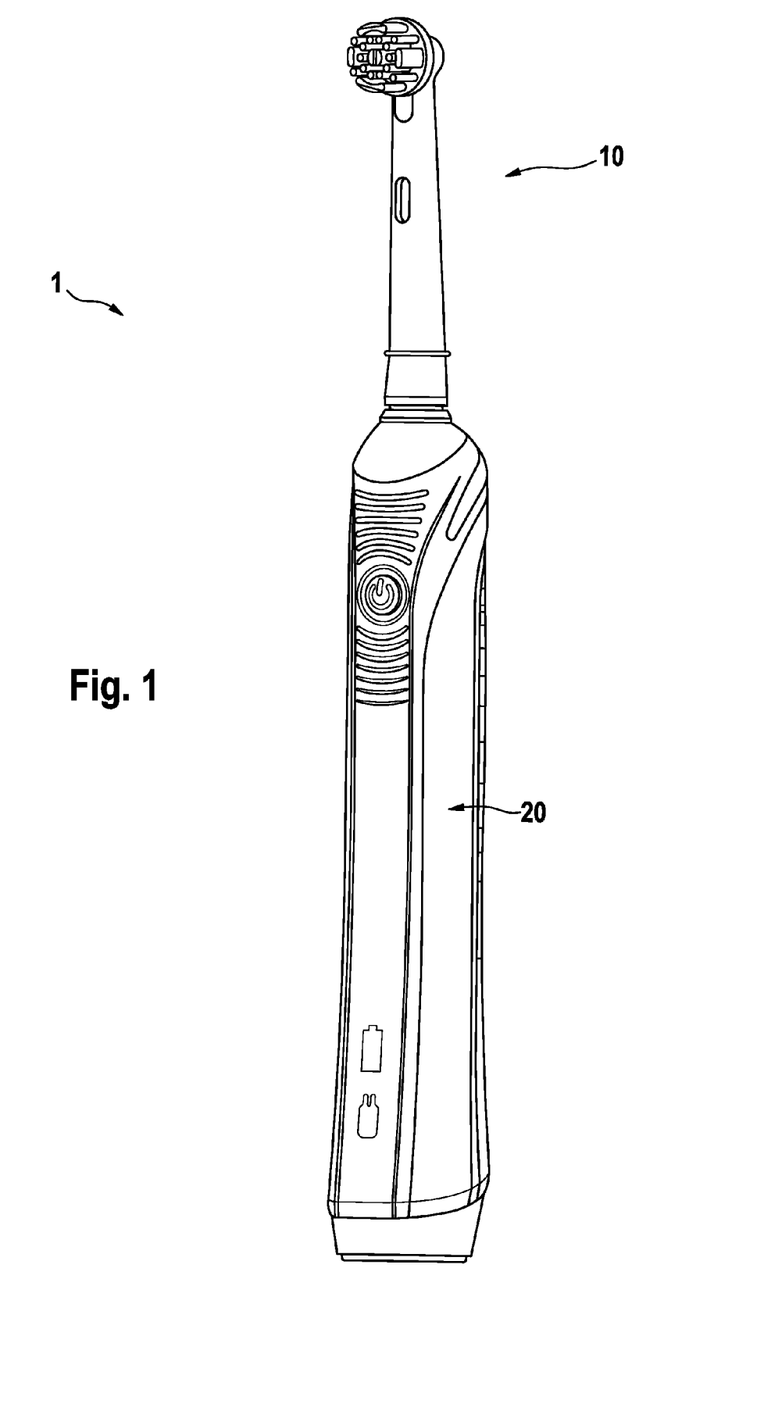
FIG. 1 is a depiction of an example embodiment of an oral care device comprising an oral care implement in accordance with the present disclosure.

FIG. 1 is a depiction of an example embodiment of an oral care device 1, here realized as an electric toothbrush. The oral care device 1 comprises an oral care implement 10 that may be integrally or detachably connected with a handle 20 (in some embodiments, a housing of the oral care implement and of the handle may be integral with each other). In the shown embodiment, the oral care implement 10 is realized as a detachable brush implement. The handle may comprise a drive and a drive shaft connected with the drive for providing a rotary or oscillatory rotary motion and which drive shaft is coupled with a functional element of the oral care device 1 (see FIG. 2) to drive the functional element into an oscillatory rotation around a rotation axis.

Figure 2:
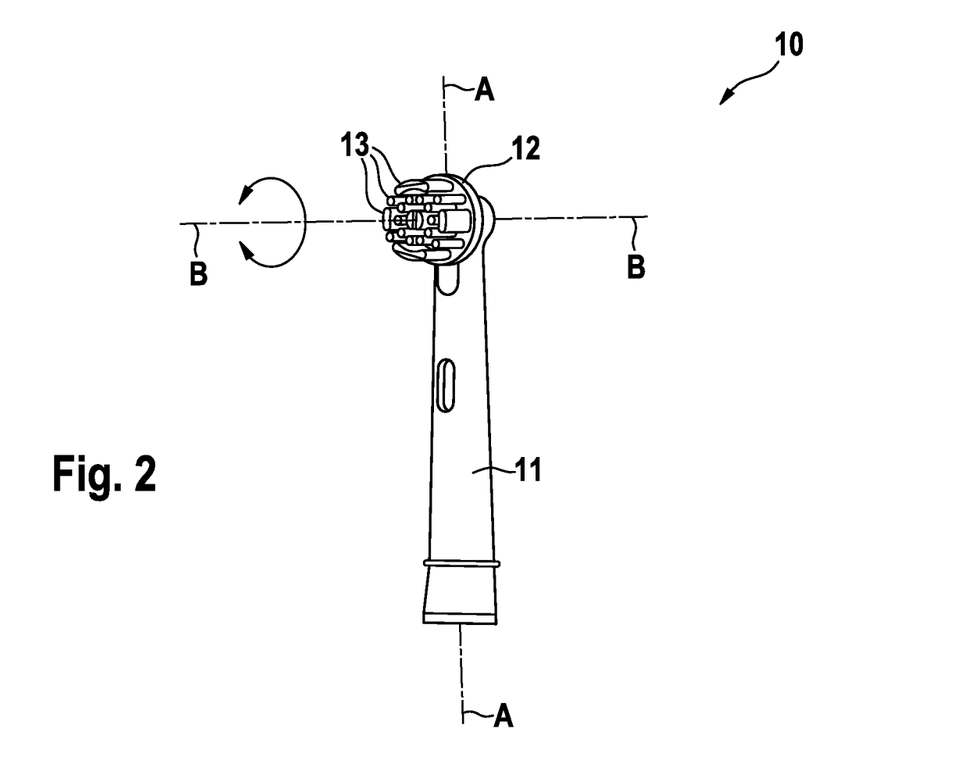
FIG. 2 is a depiction of the oral care implement shown in FIG. 1 detached from the handle of the oral care device.

FIG. 2 is a depiction of the oral care implement 10 shown in FIG. 1 being detached from the handle 20 shown in FIG. 1. The oral care implement 10, here realized as a brush implement, comprises a housing 11 and a functional element 12 mounted for driven oscillatory rotation around a rotation axis B. In the shown embodiment, the functional element 12 comprises a plurality of oral care elements 13 realized here as bristle tufts (where a tuft comprises a plurality of filaments, which may be polyamide filaments having a diameter in the range of between about 50 micrometer to about 250 micrometer, even though this should not be considered as limiting and other filaments known in the art may as well be used). Other oral care elements such as elastomeric elements (e.g. for massaging the gums) may instead be present or the functional element 12 may comprise a mixture of bristle tufts and elastomeric elements. The housing 11 of the oral care implement 10 generally extends along a longitudinal axis A. The rotation axis B may in particular be arranged with an angle to the longitudinal axis A, in particular, the rotation axis B and the longitudinal axis A may be perpendicularly arranged (i.e. at a right angle).

Figure 3A:
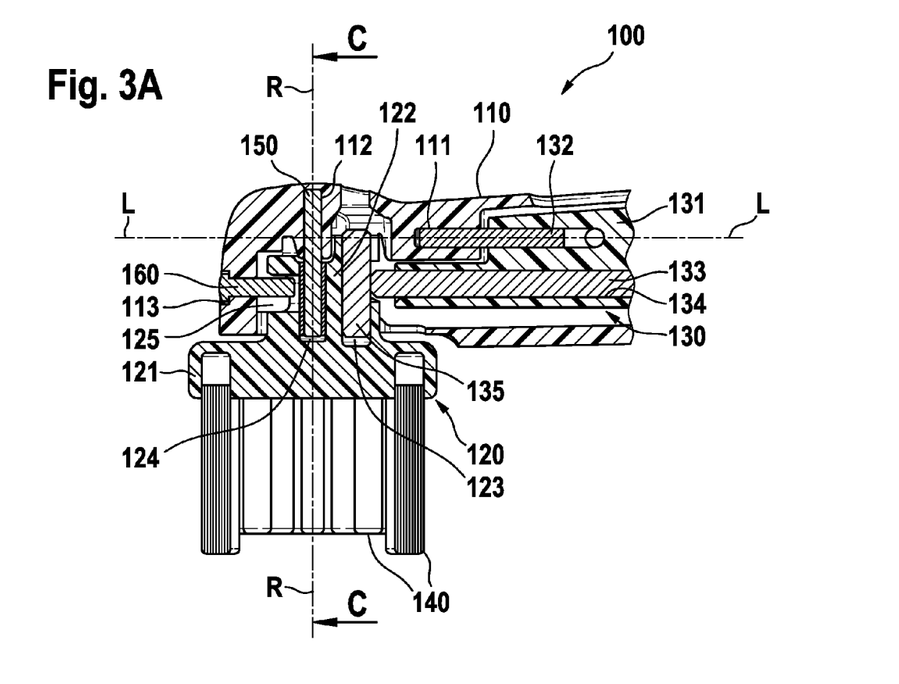
FIG. 3A is a longitudinal cut through a front portion of an example embodiment of an oral care implement in accordance with the present disclosure.
Figure 3B:
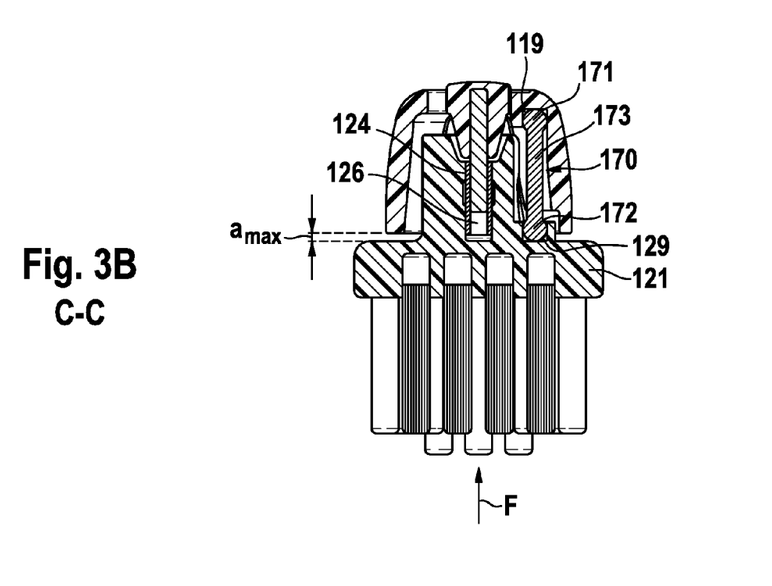
FIG. 3B is a cross section cut through the head portion of the oral care implement of FIG. 3A along line C-C shown in FIG. 3A.
Figure 3C:
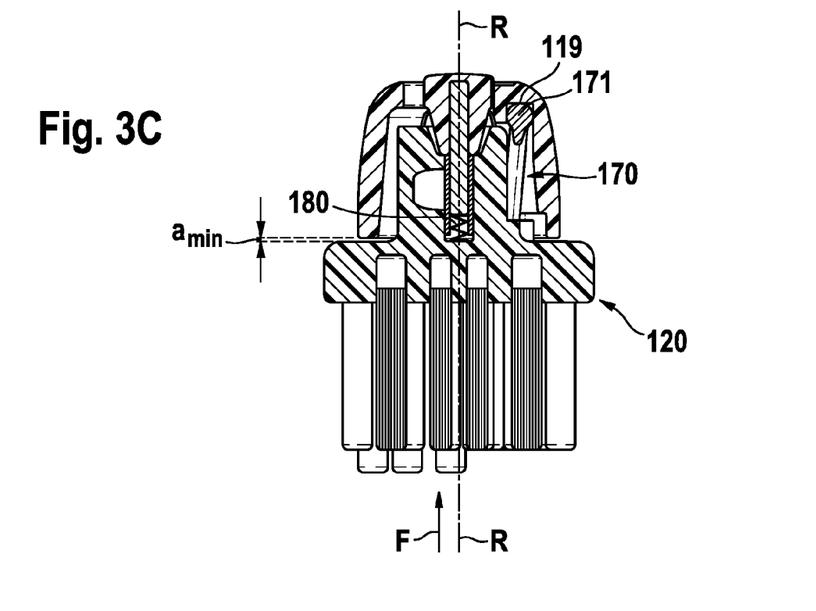
FIG. 3C is the same cross section as shown in FIG. 3B, but where the functional element was rotated to a maximum deflection angle.

FIG. 3A is a longitudinal cut through a front portion of an example embodiment of an oral care implement 100, where the longitudinal cut extends through a longitudinal axis L of the oral care implement 100 and through a rotation axis R. FIG. 3B is a cross-sectional cut through the oral care implement 100 shown in FIG. 3A along a plane indicated by line C-C in FIG. 3A. The oral care implement 100 comprises a housing 110, a functional element 120, and a rocking lever 170 (shown in FIG. 3B). FIG. 3C is the same cross-sectional cut as shown in FIG. 3B, but where the functional element 120 has been rotated to its maximum deflection angle around the rotation axis R. The functional element 120 is mounted at the housing 110 for driven oscillatory rotation around the rotation axis R. A rotation axle 150 defines the rotation axis R. The rotation axle 150 may in particular be made from metal such as stainless steel. The rotation axle 150 is borne at a respective bearing bore 112 provided in the housing and extends into a further bearing bore 124 provided in the functional element. A brass sheath or the like may be arranged (e.g. by means of jacking) in the bearing bore 124 in the functional element 120 so that the functional element 120 can rotate around the rotation axle 150 with only a low frictional loss and loss abrasion/wear of the material of the functional element 120 (the functional element 120 may in particular be made from a plastic material, e.g. in a plastic injection molding process).

The functional element 120 may comprise a carrier 121, which in particular may be a carrier disc, on which oral care elements 140 are mounted, e.g. bristle tufts for cleaning the teeth and/or elastomeric elements for massaging the gums or cleaning the tongue. Generally, the functional element 120 is coupled with a gear unit 130. In particular, the carrier 121 may be integral with a coupling element 122 for coupling the functional element 120 to the rotation axle 150 and to a gear unit 130 (see below). A locking pin 160 (in particular made from metal such as stainless steel) may be provided in a through-hole 113 in the housing 110, which locking pin 160 may extend into a cut-out 125 of the coupling element 122 to secure the functional element 120 at the housing 110 and to assure that the functional element 120 cannot be easily removed from the housing 110.

The oral care implement 100 shown in FIGS. 3A-3C comprises the gear unit 130 mentioned in the previous paragraph, which gear unit 130 is arranged to oscillate the functional element 120 around the rotation axis R. It is to be noted that this shown and discussed gear unit 130 is purely one of many possible examples and should not be interpreted as being limiting the gist and scope of the present disclosure. In some embodiments, no such gear unit may be present at all and the functional element may be directly coupled with a drive shaft. The gear unit 130 may comprise a motion transmitter 131, which may be made from a plastic material, which motion transmitter 131 may be arranged to couple with a drive shaft of a handle of an oral care device when the oral care implement 100 is attached to the handle, so that an oscillatory rotation of the drive shaft around a longitudinal axis L is transmitted by the motion transmitter 131 from the drive shaft towards the functional element 120. The gear unit 130 further may comprise a motion transmitter axle 132 for supporting the motion transmitter 131 at the housing 110 such that the motion transmitter 131 can oscillate around the longitudinal axis L. The motion transmitter axle 132 may be born at a respective bearing hole 111 provide in the housing 110. The gear unit 130 may also comprise a driving pin 133 arranged parallel to the longitudinal axis L (i.e. the driving pin 133 is then arranged eccentrically with respect to the longitudinal axis L). The driving pin 133 may in particular be born in a bore or through hole 134 in the motion transmitter 131 so that it can oscillate around its longitudinal axis and can linearly move in the bore or through-hole 134. When the motion transmitter 131 is oscillated around the longitudinal axis L, the driving pin 133 moves along an arc around the longitudinal axis L. The driving pin 133 may be coupled to the functional element by a T-bar element 135 that is secured (e.g. welded) to an end of the driving pin 133. The T-bar element 135 may be born in a respective mounting bore 123 provided in the functional element 120 eccentric to the rotation axis R so that the T-bar element is fixedly secured at the functional element 120 with respect to the longitudinal direction but is moveable in a direction parallel to the rotation axis R. As the driving pin 133 moves along an arc around the longitudinal L, the T-bar element 135 moves up and down in the mounting hole 123 (while at the same time the T-bar element 135 as part of the driving pin 133 carries the functional element 120 along) and the driving pin 133 rotates in the bore or through-hole 134. As the driving pin 133 moves along an arc around the longitudinal axis L it also acts eccentrically with respect to the rotation axis R at the functional element 120 and thereby oscillates the functional element 120 around the rotation axis R.

As can be seen in FIG. 3B, the oral care implement 100 comprises a rocking lever 170. While in FIG. 3B only one such rocking lever 170 is shown, this shall not exclude that at least a second rocking lever is present as well (which second rocking lever may in particular be arranged symmetrically on the opposite side of the functional element with respect to the rotation axis, as is discussed for a particular embodiment with respect to FIGS. 6A and 6B). Generally (i.e. not limited by the shown embodiment), the rocking lever has a first end 171 and a second end 172 and a main leg 173 extending in between the first end and the second end. In the shown embodiment, the rocking lever 170 has a bone-shaped form, but this shall not be interpreted as limiting and the rocking lever 170 may have any other suitable form, of which a few are described further below. In embodiments, where the rocking lever 170 has a bone-shaped form, it may have a central straight leg 173 and two thickenings 171 and 172 at the respective opposite first and second ends of the rocking lever 170. The thickenings 171 and 172 may in particular be essentially spherical thickenings. Generally (i.e. not limited to the shown embodiment), the rocking lever 170 is at its first end 171 supported at the housing 110 at an essentially fixed position eccentric to the rotation axis R, where here a mounting bore 119 is provided in the housing 110. Due to the essentially spherical thickening of the shown embodiment at the first end 171 of the rocking lever 170, the rocking lever 170 can pivot with respect to its bearing position realized here by the bearing bore 119. The bearing position of the first end 171 of the rocking lever 170 at the housing is eccentric with respect to the rotation axis R. Further generally (i.e. not limited by the shown embodiment), the second end 172 of the rocking lever 170 is coupled with the functional element 120 at an essentially fixed position eccentric with respect to the rotation axis R. In the shown embodiment, the essentially spherically thickened second end 172 of the rocking lever 170 is accommodated within a mounting bore 129 in the functional element 120.

FIG. 3B shows a state where the rocking lever 170 extends parallel to the rotation axis R and thus defines (or enforces) a maximum distance $a_{max}$ between the functional element 120 and the housing 110. That means that even under application of an external force F (e.g. a brushing force applied during operation) acting on the functional element 120 in the direction of the rotation axis R, the rocking lever 170 inhibits that the distance $a_{max}$ between functional element 120 and housing 110 becomes any smaller. Instead of being parallel to the rotation axis R, the rocking lever may also be inclined with respect to the rotation axis even when it defines the maximum distance between housing and functional element. The rocking lever 170 may be made from metal such as stainless steel; even though this shall not be considered as limiting and the rocking lever may be made from a plastic material (reference is made to the discussion of FIGS. 6A and 6B below).

FIG. 3C shows a state where the motion transmitter 131 (FIG. 3A) was oscillated to its maximum deflection angle around the longitudinal axis L (which maximum deflection angle may have any suitable value, even though values in the range of between 20 degrees to 40 degrees may in particular be considered). This oscillation of the motion transmitter 131 has as a result also led to an oscillation of the functional element 120 around the rotation axis R to a maximum deflection angle. As the second end 172 of the rocking lever 170 is borne in the mounting bore 129, which mounting bore 129 rotates together with the functional element 120, while the respective mounting bore 119 in the housing 110, in which the first end 171 of the rocking lever 170 is borne, remains static (as the housing remains static), the second end 172 of the rocking lever is carried along by the functional element 120 and the rocking lever 170 is moved into an inclined position, which also means that the rocking lever now defines a minimum distance $a_{min}$ between housing 110 and functional element 120. Given the usual dimensions of oral care implements and given the typical maximum deflection angles provided by drive shafts of handles of typical oral care devices, a stroke distance of about $|a_{max}-a_{min}|=0.2$ mm can be achieved (even though, this value shall not be considered as limiting as, obviously, the dimensions and angles can be tuned to achieve any other sensible value). This means that the functional element 120 is arranged to not only oscillate around rotation axis R during operation but that the functional element 120 will also perform a poking motion (i.e. a linearly oscillating motion) in the direction of the rotation axis R during operation. In case the maximum distance $a_{max}$ is reached when the motion transmitter 131 is in its center oscillation position, then the frequency of the poking motion is twice the frequency of the oscillation motion as the minimum distance $a_{min}$ will then be reached at the maximum deflection angle in both rotation directions (i.e. in clockwise and in anti-clockwise direction) around rotation axis R. In case the oral care implement 100 is arranged such that the maximum distance $a_{max}$ is reached at a maximum oscillation position (i.e. at maximum deflection angle) in one direction and the minimum $a_{min}$ distance is achieved at maximum deflection angle in the opposite direction, then the frequency of the poking motion is identical to the oscillation frequency.

In order to allow for the change in distance between housing and functional element, the rotation axle 150 may not fully extend into bore 124 as is shown in FIG. 3B, where a headroom 126 is provided that can accommodate the respective movement, so that the functional element 120 can be pushed towards the housing 110 (a channel may be provided e.g. in the rotation axle 150 to allow for air flow). Alternatively or additionally, at least one spring element 180 may be provided between the housing 110 and the functional element 120 (in FIG. 3C this spring element 180 is arranged at the location of the headroom 126 shown in FIG. 3B, but any suitable position between housing and functional element may be chosen). The spring element 180 may be biased such that it will contract when the distance between housing 110 and functional element 120 becomes lower than $a_{max}$.

Then, as the rocking lever 170 itself does in the shown embodiment not pull the functional element 120 towards the housing 110, the spring element 180 will force this movement even without any external force F (i.e. even in an idle operation). In other embodiments, the spring element 170 is biased such that it keeps the maximum distance $a_{max}$ even when the functional element 120 rotates and the rocking lever 170 inclines. Then the poking motion only occurs under an external brushing force F that overcomes the respective spring force component acting in the rotation axis direction. This latter arrangement may reduce noise during idle operation as then the poking motion is suppressed.

Figure 4:
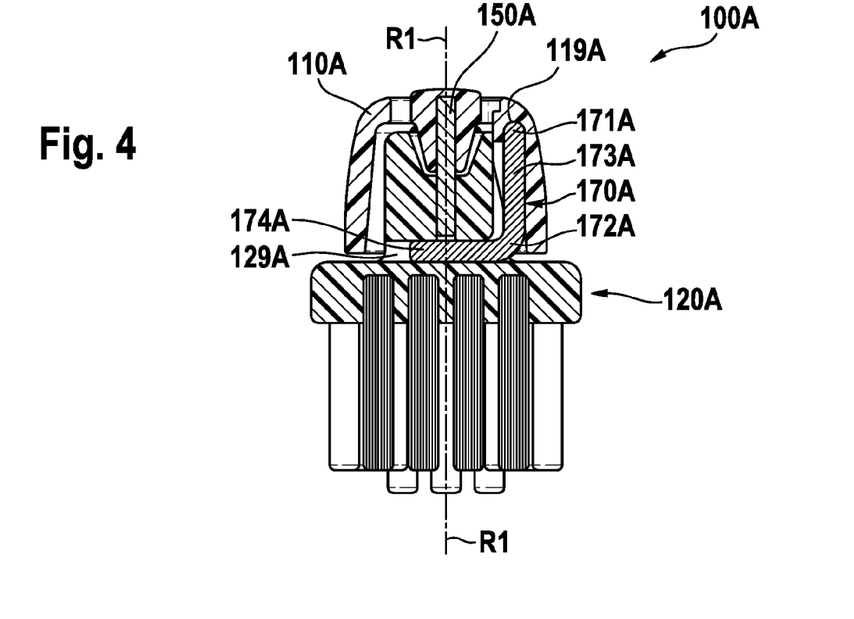
FIG. 4 is a cross section as shown in FIG. 3B through another example embodiment of an oral care implement in accordance with the present disclosure.

FIG. 4 is a cross-sectional cut similar to FIG. 3B, but through the head of another example embodiment of an oral care implement 100A in accordance with the present disclosure. The oral care implement 100A comprises a housing 110A and a functional element 120A similar to what was described with respect to FIGS. 3A-3C. The same gear unit as described before may be used in oral care implement 100A. The oral care implement 100A comprises a rocking lever 170A that has a first end 171A and a second end 172A. The first end 171A is hemispherically rounded and is supported in a respective bearing bore 119A in housing 110A. Alternatively, the first end of the rocking lever may also comprise a spherical thickening as previously discussed. The shown bearing bore 119A is tapered so that the rocking lever 170A can pivot in bearing bore 119A when the functional element 120A is driven into oscillatory rotation. The second end 172A of the rocking lever 170A comprises a crossbeam arm 174A that extends at a right angle from a central leg 173A of the rocking lever 170A. The crossbeam arm 174A extends into a bore or through-hole 129A provided in the functional element 120A. The crossbeam arm 174A here crosses the rotation axis R1. When the functional element 120A is now rotated out of the shown position, the rocking lever 170A is moved into an inclined position. Under application of an external force, the functional element 120A is pulled towards the housing by the inclining rocking lever 170A. A spring element may additionally be provided as was discussed with reference to the previous example embodiment. In an embodiment as shown, the force that acts of the functional element 120A is applied not only at a single point as in the embodiment shown in FIGS. 3A-3C but the force is applied along the crossbeam arm 174A which here extends to both sides of the rotation axis R1, so that a possible jamming of the functional element 120A on the rotation axle 150A is effectively reduced. It is to be noted that the second end 172A of the rocking lever 170A is again coupled with the functional element 120A at a position that is eccentric with respect to the rotation axis R1 as for the determination of the distance between housing 100A and functional element 120A just the main leg 173A is relevant and thus it is relevant where the main leg 173A ends, which is at a position eccentric to the rotation axis R1.

Figure 5A:
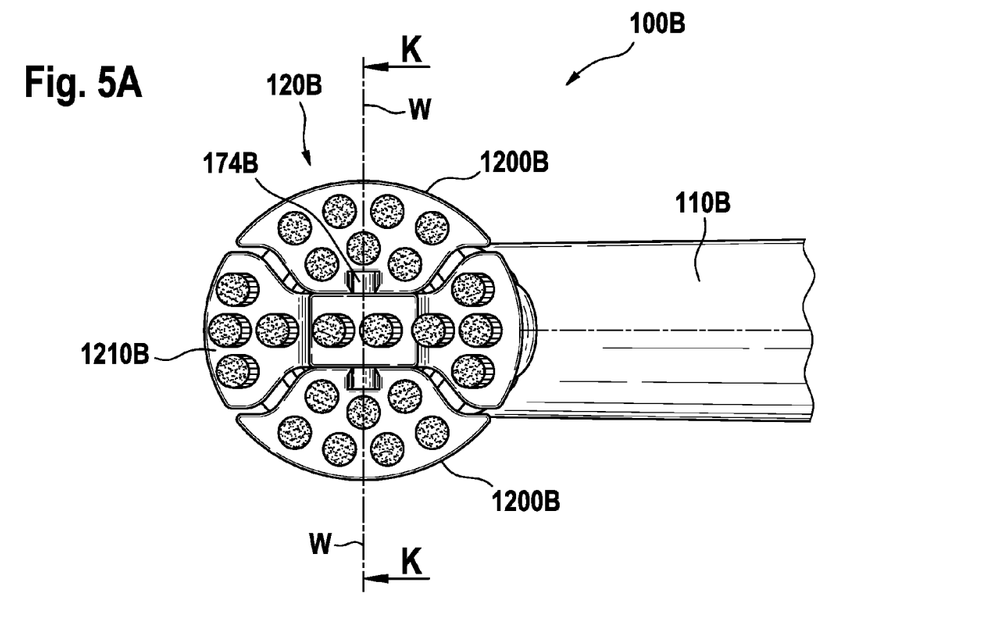
FIG. 5A is a top view onto a front portion of a further example embodiment of an oral care implement in accordance with the present disclosure.
Figure 5B:
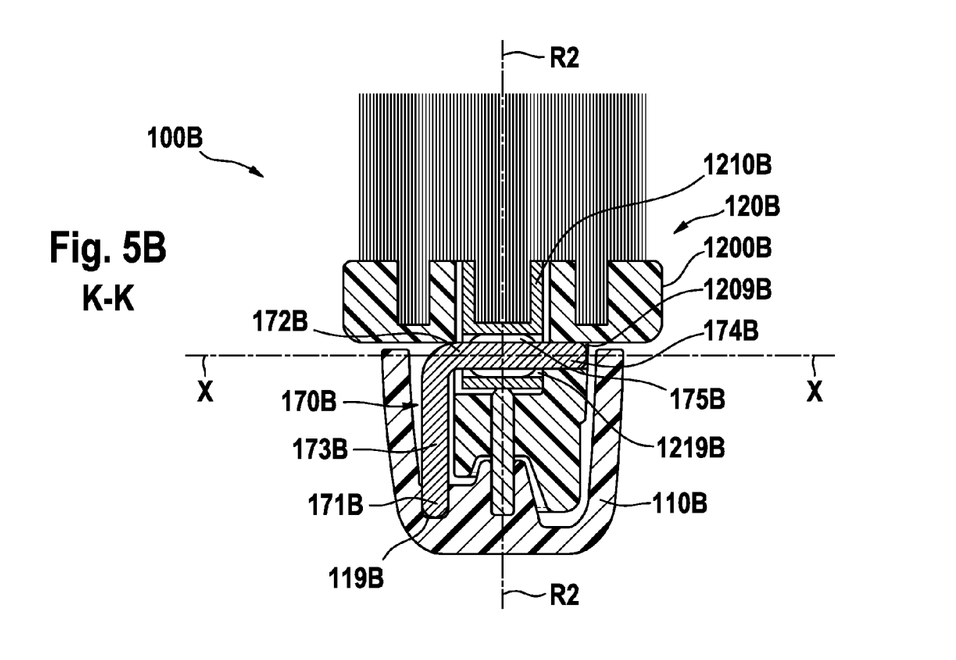
FIG. 5B is a cross sectional cut through the head portion of the oral care implement shown in FIG. 5A.

FIG. 5A is a top view onto a further example embodiment of an oral care implement 100B in accordance with the present disclosure. The oral care implement 100B comprises a housing 110B and a functional element 120B mounted at the housing for driven oscillatory rotation around a rotation axis R2 (FIG. 5B). The functional element 120B here comprises a static part 1200B and an active part 1210B (also: rocker part), which active part 1210B is mounted for rocking movement around rotation axis W. The active part 1210B is mounted on a shaft that is realized by a crossbeam arm 174B of a rocking lever 170B as will become clear from below description with reference to FIG. 5B. Thus, while the whole functional element 120B will perform an oscillating rotation and a poking motion as previously explained, the active part 1210B will additionally perform a rocking motion around rotation axis W. An oral care implement similar to the shown oral care implement 120B (but without a rocking lever and associated poking motion) is discussed in document EP 1 093 770 A2, which document is incorporated herein by reference.

FIG. 5B shows a cross sectional cut through the oral care implement 100B along line K-K as indicated in FIG. 5A. Again, the oral care implement 100B comprises a rocking lever 170B for inducing the previously explained poking motion along rotation axis R2. The rocking lever 170B is shown in its maximum elongation state with respect to the rotation axis direction so that any rotation of the functional element 120B out of the shown position will result in an inclination and pivoting of the rocking lever 170B that so that the functional element 120B is moved towards the housing 110B. The first end 171B of the rocking lever 170B is again hemisperically rounded and the first end 171B is supported in a tapered bearing bore 119B provided in the housing 110B. As before, this shall not be considered as limiting and the first end of the rocking lever may have any other suitable form. A second end 172B of the rocking lever 170B is coupled with the functional element at an essentially fixed position that is eccentric with respect to the rotation axis R2. The second end 172B further comprises a crossbeam arm 174B that extends at a right angle from a central leg 173B of the rocking lever 170B. The crossbeam arm 174B is supported in a bore or through-hole 1209B provided in the static part 1200B of the functional element 120B. The crossbeam arm 174B also extends through a through-hole 1219B provided in the active part 1210B of the functional element 120B. The crossbeam arm 174B crosses the rotation axis R2 around which the functional element 120B can be driven into an oscillatory rotation. The crossbeam arm 174B comprises an undercut section 175B that cooperates with a respective portion of the through-hole 1219B of the active part 1210B so that the crossbeam arm 174B cannot rotate in the through-hole 1219B, while the crossbeam arm 174B can rotate in the bore 1209B provided in the static part 1200B of the functional element 120B. Thus, when the functional element 120B is rotated around the rotation axis R2 out of the shown position, the rocking lever 170B will tilt and pivot in bearing bore 119B and the crossbeam arm 174B will then, as a consequence of the tilting motion, also rotate around its longitudinal axis X. As the crossbeam arm 174B cannot rotate in through-hole 1219B due to the undercut section 175B, the active portion 1210B is forced to rotate together with the crossbeam arm 174B around axis X. Depending on the details of the set-up of the respective realization of this example embodiment, oscillation angles around axis X from about 5 degree to about 20 degrees may be achieved (even though these value shall not be considered as limiting).

Figure 6A:
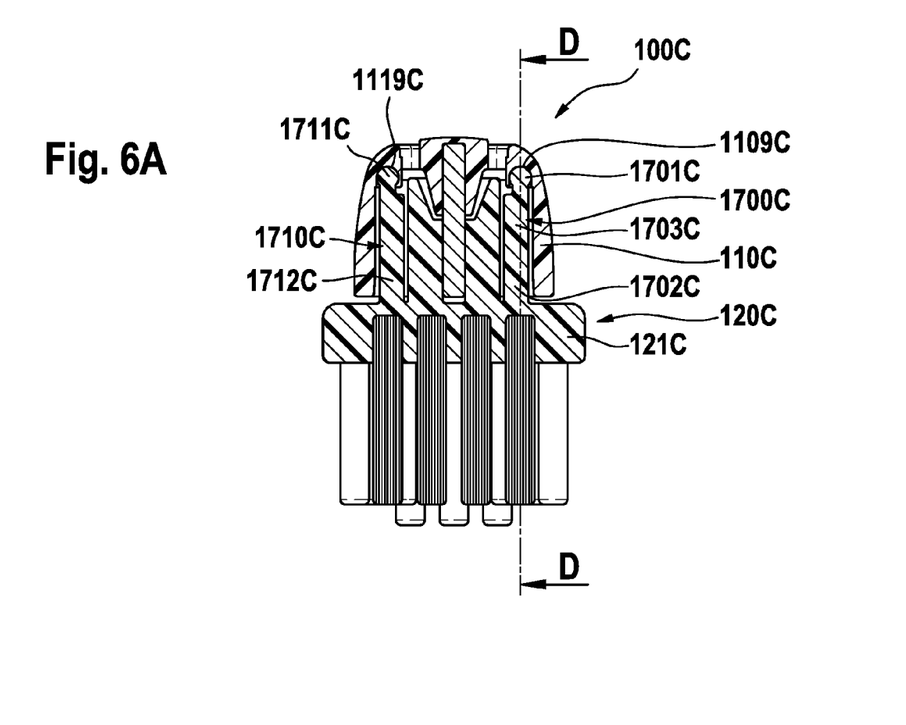
FIG. 6A is a cross sectional cut through an even further example embodiment of an example embodiment of an oral care implement in accordance with the present disclosure.

FIG. 6A is a cross sectional cut through a head section of an even further example embodiment of an oral care implement 100C in accordance with the present disclosure. The oral care implement 100C comprises a housing 110C, a functional element 120C, and two rocking levers 1700C and 1710C. In the shown example embodiment, the rocking levers 1700C and 1710C are realized integral with the functional element 120C, e.g. they may be jointly injection molded together with the functional element 120C or at least with a carrier 121C of the functional element 120C. Each of the rocking levers 1700C, 1710C has a respective first end 1701C and 1711C that is realized as a spherically thickened portion that can pivot in a respective supporting hole 1109C and 1119C provided in the housing 110C. It is noted that this integral connection of a rocking lever and a functional element is a "coupling" between these two elements in accordance with the present disclosure. The use of two rocking levers may result in a more symmetric application of force with respect to the rotation axis when the rocking levers are raised from their inclined position, resulting in a lower probability of canting of the functional element on the rotation axle. It is noted that it shall not be excluded that additionally or alternatively the rocking lever is made integral with the housing.

Figure 6B:
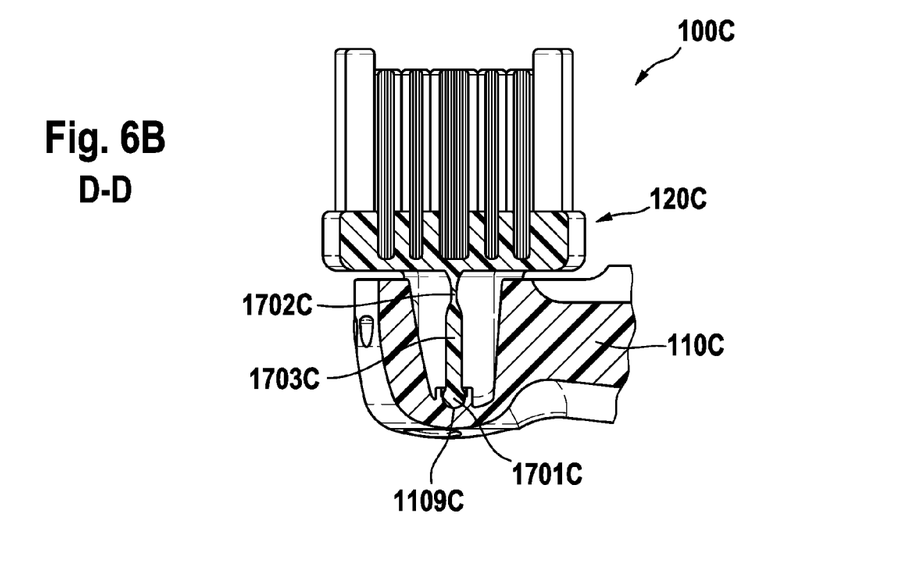
FIG. 6B is a longitudinal through a front portion of the oral care implement shown in FIG. 6A, where the cut goes through line D-D indicated in FIG. 6A.

FIG. 6B is a longitudinal cut through the head portion of the oral care implement 100C taken along line D-D indicated in FIG. 6A. It can be seen that the second end 1702C of the rocking lever 1700C is arranged as a hinge, in particular as a living hinge so that pivoting of the rocking lever 1700C relative to the functional element 120C is enabled. In embodiments, where the rocking lever is made integral with the housing, the first end may be realized as a hinge.

An embodiment as discussed with reference to FIGS. 6A and 6B tends to be cheaper realizable than an embodiment with a separate rocking lever as the here the rocking lever is simply provided by the plastic injection molding step by which also at least the carrier 121C of the functional element 120C is made. Further, the assembly becomes simpler as no separate rocking lever needs to be handled.

In alternative embodiments, a rocking lever similar in structure to the rocking lever 1700C shown in FIGS. 6A, 6B may be injection molded as a separate part, which allows using a plastic material for the rocking lever that is optimal for realizing a living hinge such as polyethylene (PE), which rocking lever could then be secured at the functional element by e.g. a snap fit, gluing or welding or any other suitable method. In further alternative embodiments, the functional element (or at least a carrier of the functional element) and at least one rocking lever could become injection molded in a two-component injection molding process. In particular, two non-affine plastic materials (i.e. plastic materials that do not bond to each other in the molding process) such as polyoxymethylene (POM) and polyamide (PA) could be chosen. In the two-component injection molding process, first the functional element (or at least the carrier) would be molded using the first plastic material, where the carrier has an undercut bearing hole (or holes), and then the rocking lever(s) would be molded with the undercut bearing hole(s) defining part of the cavity for molding the rocking lever(s). As the two plastic materials are chosen such that they do not adhere to each other, the rocking lever(s), in particular after the shrinking process during cooling, could pivot in the respective undercut bearing hole(s). As the bearing hole(s) were provided as undercut bearing holes (e.g. they may widen spherically), the rocking lever(s) are then pivotably connected with the functional element and cannot be separated from the functional element without at least partially destroying either the rocking lever or the functional element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A toothbrush head comprising:
   a housing;
   a functional element mounted at the housing for driven oscillatory rotation relative to the housing around a rotation axis and a poking motion in a direction substantially parallel to the rotation axis;
   at least one rocking lever having a first end and a second end opposite to the first end, the first end being pivotably supported at the housing at an essentially fixed position that is eccentric with respect to the rotation axis and the second end being coupled with the functional element at a position eccentric with respect to the rotation axis such that the functional element carries the second end of the rocking lever along when it is driven into oscillatory rotation around the rotation axis, while the first end of the rocking lever is kept at its fixed position at the housing, and wherein the at least one rocking lever is disposed in the direction essentially parallel to the rotation axis.

2. The toothbrush head in accordance with claim 1, wherein the rocking lever has its maximum length in the direction essentially parallel to the rotation axis when the functional element is in a center oscillation position between the maximum elongations in positive and negative oscillation direction.

3. The toothbrush head in accordance with claim 1, wherein the rocking lever has its maximum length in the direction essentially parallel to the rotation axis when the functional element is in an oscillation position of maximum elongation in a condition where no load is applied at the functional element.

4. The toothbrush head in accordance with claim 1, wherein a spring element is arranged between the housing and the functional element, wherein the spring element has at least a spring force component acting in a direction parallel to the rotation axis.

5. The toothbrush head in accordance with claim 1, wherein at least one of the first end and the second end of the rocking lever has an essentially spherical thickening.

6. The toothbrush head in accordance with claim 1, wherein the second end of the rocking lever is integrally connected with the functional element and comprises a living hinge.

7. The toothbrush head in accordance with claim 6, comprising two rocking levers, each of which is integrally connected with the functional element.

8. The toothbrush head in accordance with claim 1, wherein the rocking lever is an injection-molded part, and wherein the functional element and the rocking lever are only destructively separable.

9. The toothbrush head in accordance with claim 1, wherein the head is structured and configured to be connected to a handle of an electric toothbrush.

10. The toothbrush head in accordance with claim 9, wherein the head is structured and configured to be integrally connected to the handle of the electric toothbrush.

11. The toothbrush head in accordance with claim 9, wherein the head is structured and configured to be detachably connected to the handle of the electric toothbrush.

12. An electric toothbrush comprising the toothbrush head in accordance with claim 1.

13. An electric toothbrush comprising the toothbrush head in accordance with claim 11.

* * * * *